(12) United States Patent
Min et al.

(10) Patent No.: US 10,890,972 B2
(45) Date of Patent: Jan. 12, 2021

(54) PREFRONTAL-BASED COGNITIVE BRAIN-MACHINE INTERFACING APPARATUS AND METHOD THEREOF

(71) Applicant: KOREA UNIVERSITY RESEARCH AND BUSINESS FOUNDATION, Seoul (KR)

(72) Inventors: Byoung-Kyong Min, Seoul (KR); Kyuwan Choi, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 364 days.

(21) Appl. No.: 15/946,882

(22) Filed: Apr. 6, 2018

(65) Prior Publication Data

US 2018/0292902 A1 Oct. 11, 2018

(30) Foreign Application Priority Data

Apr. 6, 2017 (KR) ........................ 10-2017-0044695
Mar. 20, 2018 (KR) ........................ 10-2018-0032121

(51) Int. Cl.
*G06F 3/01* (2006.01)
*A61B 5/0482* (2006.01)
(Continued)

(52) U.S. Cl.
CPC ............ *G06F 3/015* (2013.01); *A61B 5/0478* (2013.01); *A61B 5/0482* (2013.01);
(Continued)

(58) Field of Classification Search
CPC ....... A61B 5/16; A61B 5/0478; A61B 5/4064; A61B 5/0482; A61B 5/048; G06F 3/015
See application file for complete search history.

(56) References Cited

U.S. PATENT DOCUMENTS

| 5,325,862 A * | 7/1994 | Lewis ................. A61B 5/1171 600/544 |
| 2014/0020089 A1* | 1/2014 | Perini, II ................. G07C 9/37 726/19 |
| 2016/0038049 A1* | 2/2016 | Geva ................. A61N 1/36135 600/544 |

FOREIGN PATENT DOCUMENTS

KR 10-1518575 B1 5/2015

OTHER PUBLICATIONS

Min, Byoung-Kyong, et al., "Harnessing Prefrontal Cognitive Signals for Brain-Machine Interfaces," *Trends in Biotechnology*, Apr. 2017, pp. 1-13.

* cited by examiner

*Primary Examiner* — Christine H Matthews
*Assistant Examiner* — Joshua Daryl D Lannu
(74) *Attorney, Agent, or Firm* — NSIP Law

(57) ABSTRACT

Provided are prefrontal-based brain-machine interfacing apparatus and a method thereof. The apparatus includes a brainwave measurement device configured to measure a prefrontal brainwave signal of a subject, and a processor configured to execute a cognitive brain-machine interface program stored in a memory, the processor pinpoints a brain cortical region generating the corresponding prefrontal brainwave signal among previously assigned multiple subdivisions of a prefrontal area, measures the sensor-level brain activity, extracts a prefrontal cortical-level activity pattern by computing source localization and calculating causal connectivity among two or more previously assigned brain regions on the basis of the degree of corresponding sensor-level brain activities, inputs the prefrontal activity pattern into a classifier which is previously generated by machine learning of multiple prefrontal activity patterns of the subject to identify one of the preset control conditions, (Continued)

and generates and outputs a preset machine regulating signal on the basis of a result of identification.

14 Claims, 7 Drawing Sheets

(51) Int. Cl.
  *A61B 5/0478* (2006.01)
  *A61B 5/00* (2006.01)
  *A61B 5/16* (2006.01)
  *A61B 5/048* (2006.01)
(52) U.S. Cl.
  CPC ............ *A61B 5/4064* (2013.01); *A61B 5/048* (2013.01); *A61B 5/16* (2013.01)

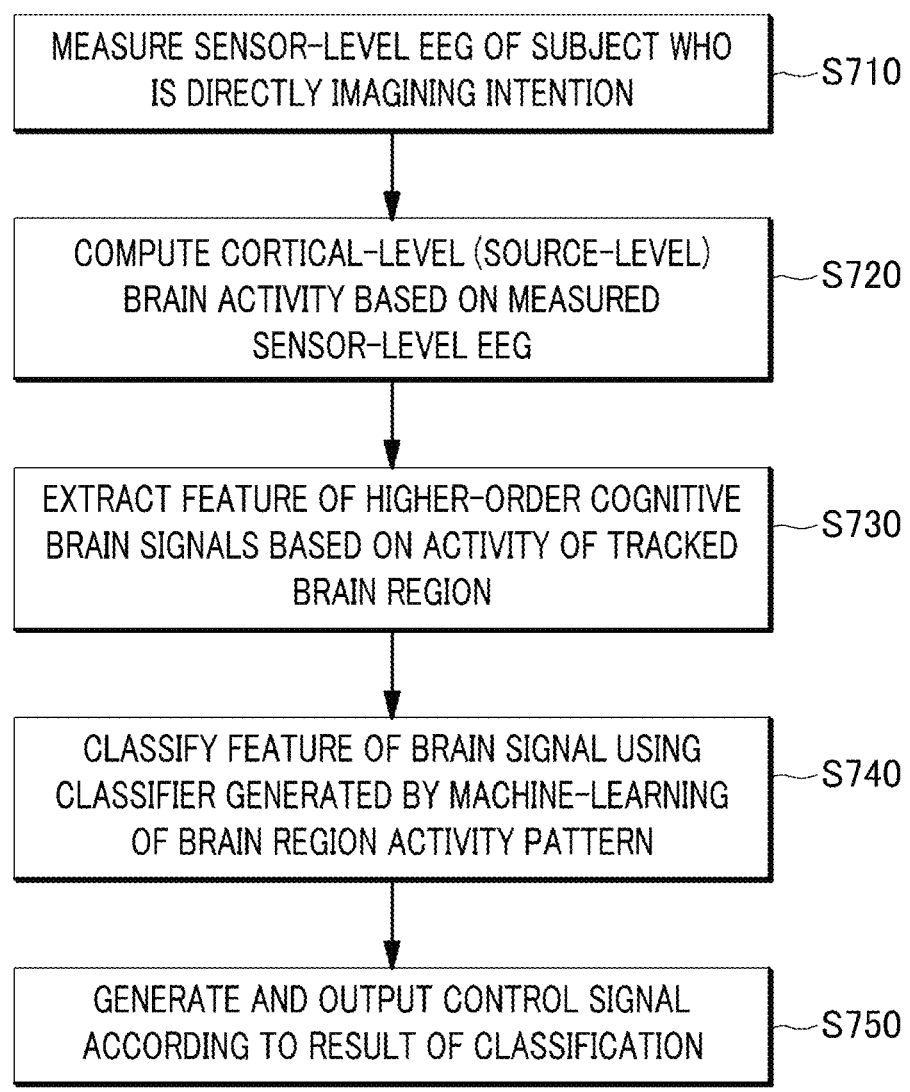

PREFRONTAL-BASED COGNITIVE BRAIN-MACHINE INTERFACING APPARATUS AND METHOD THEREOF

CROSS-REFERENCE TO RELATED APPLICATION

This application claims the benefit under 35 USC 119(a) of Korean Patent Application No. 10-2017-0044695 filed on Apr. 6, 2017, and Korean Patent Application No. 10-2018-0032121 filed on Mar. 20, 2018, in the Korean Intellectual Property Office, the entire disclosures of which are incorporated herein by reference for all purposes.

TECHNICAL FIELD

The present disclosure relates to an apparatus and method for processing brain-machine interface (BMI), and more particularly, to a cognitive brain-machine interfacing apparatus using a brainwave signal from a prefrontal area and a method thereof.

BACKGROUND

Studies on brain-machine interface (BMI) technology for controlling a machine or brain-computer interface (BCI) technology for controlling a computer according to the intention of a person by using a brainwave signal are being actively conducted. Particularly, technologies of processing brain-machine interfaces by analyzing parameters caused by cognitive features of brainwave signals have been developed.

In this regard, Korean Patent No. 10-1518575 (entitled "Analysis method of user intention recognition for brain-computer interface") discloses a method including: acquiring a user's brainwave data measured by a brainwave measurement device in a preprocessing unit; converting the brainwave data into a frequency signal and classifying a frequency domain relevant to a sense of movement according to a bandwidth of the converted frequency signal in an identification unit; detecting the user's intention recognition from the brainwave data in the frequency domain by analyzing a feature that appears depending on the user's motor imagery in a detection unit, and displaying a result of detection of the intention recognition in a display unit to enable the user to check the result. Specifically, Korean Patent No. 10-1518575 discloses an analysis method of user intention recognition in which the brainwave data are brainwave signals measured by attaching 14-channel electrodes having a sampling rate of 128 SPS (2048 Hz) to the user, and the electrodes are attached to 14 locations on the scalp: AF3, F7, F3, FC5, T7, P7, O1, O2, P8, T8, FC6, F4, F8, AF4, according to the International 10-20 electrode system, and when a frequency domain relevant to a sense of movement is classified, a digital notch filter (DNF) is used to classify a brainwave mu rhythm ($\mu$) area.

As such, most of the conventional BMI (or BCI) technologies have used brainwave signals from the occipital lobe or parietal lobe. However, it is difficult to classify and express various human intentions by the intention recognition method based on brainwave signals from the occipital or parietal areas, and the kinds of usable BMI control signals principally based on those areas are limited. In addition, the intention recognition method using brainwave signals from the occipital or parietal areas cannot match the content of the user's thinking with a goal-orientation of BMI control.

Higher-order cognitive functions of human beings occur in a frontal area (more specifically, prefrontal area) of the brain. Therefore, if brainwave signals from this area of the brain are used as BMI (or BCI) signals, it is possible to recognize and classify the user's higher-order intentions. Thus, one's various higher-order cognitive features from the frontal brain area can be used as BMI control signals that could make more multi-class repertoires of BMI signals available. For example, the frontal area of the human brain is in charge of decision-making, and if the feature of one's intention is detected as a brainwave signal of the frontal area, it is possible to directly match the featured brainwave signal with a goal-direction of BMI control. Therefore, a BMI technology capable of higher-order intention recognition based on brainwave signals from the frontal area is needed.

Meanwhile, brainwaves are important bio-signals showing an activity and ongoing status of the human brain. The brainwaves show an increase or decrease in oscillations depending on the kind of ongoing cognitive functions. However, if a function of the brain is abnormal (e.g., an attention deficit disorder (ADD) patient or a case of low IQ), brainwaves are slow as compared with those of a normal person. Further, various abnormal brainwaves may occur depending on the kind of disease. For example, epilepsy shows a strong brainwave of 3 Hz and all of autism, mental retardation, attention deficit/hyperactivity disorder (ADHD), attention deficit disorder (ADD) and dementia show very robust theta waves. Further, in the case of depression, the right brain shows brainwaves with faster rhythms than the left brain.

As a technology for controlling such abnormal rhythms of the brain to be normal, biofeedback technology is being developed. Particularly, biofeedback for controlling brainwaves is referred to as neurofeedback formed by adding the prefix "neuro-" meaning "related to nerve". The need for BMI (or BCI) technology applicable to neurofeedback rehabilitation has been highly increased. Accordingly, the development of a BMI technology capable of higher-order intention recognition and also applicable to neurofeedback rehabilitation is needed.

SUMMARY

In view of the foregoing, the present disclosure provides a prefrontal-based cognitive brain-machine interfacing apparatus for processing frontal brainwave signals as cognitive brain-machine interfacing control signals and a method thereof.

Further, the present disclosure provides a brain-machine interfacing apparatus that can apply processing of cognitive brain-machine interfacing using a frontal brainwave signal to neurofeedback rehabilitation and a method thereof.

However, problems to be overcome by the present disclosure are not limited to the above-described problems. There may be other problems to be solved by the present disclosure.

According to an aspect of the present disclosure, a prefrontal-based cognitive brain-machine interfacing apparatus includes: a brainwave measurement device configured to disentangle a prefrontal brainwave signal of a subject; a memory in which a cognitive brain-machine interface program is stored; and a processor configured to execute the program stored in the memory. Herein, upon execution of the cognitive brain-machine interface program, the processor pinpoints a brain cortical region generating the corresponding prefrontal brainwave signal among previously assigned multiple subdivisions of a prefrontal area, measures the degree of corresponding sensor-level brain activities, extracts a prefrontal cortical-level (or source-level) activity pattern by computing source localization and calculating causal connectivity among two or more previously assigned brain regions (e.g. Brodmann areas) on the basis of the degree of corresponding sensor-level brain activity, inputs the extracted prefrontal activity pattern into a classifier which is previously generated by machine learning of multiple prefrontal activity patterns of the subject to identify any of preset control conditions corresponding to the extracted prefrontal activity pattern among the preset (labelled) brain-machine interface control conditions, and generates and outputs a machine regulating signal corresponding to one of the preset control conditions identified by the classifier. Herein, the classifier is generated by machine learning of the prefrontal activity patterns labelled for contents of multiple intentions, respectively, on the basis of prefrontal brainwave signals of the subject.

According to another aspect of the present disclosure, a prefrontal-based cognitive brain-machine interfacing method includes: receiving sensor-level brainwave signals of a subject from a brainwave measurement device; recognizing a cortical-level (or source-level) brain region corresponding to the prefrontal brainwave signal among previously assigned multiple subdivisions of a prefrontal area; extracting a prefrontal activity pattern by measuring the degree of corresponding brain activities and calculating causal connectivity among two or more previously assigned brain regions on the basis of the corresponding sensor-level brain activity; inputting the extracted prefrontal activity pattern into a classifier which is previously generated by machine learning of multiple prefrontal activity patterns of the subject to identify any of preset control conditions corresponding to the extracted prefrontal activity pattern among the preset brain-machine interface control conditions; and generating and outputting a machine regulating signal corresponding to one of the preset control conditions identified by the classifier. Herein, the classifier is generated by machine learning of the prefrontal activity patterns labelled for contents of multiple intentions, respectively, on the basis of prefrontal brainwave signals of the subject.

According to any one of the above-described aspects of the present disclosure, a control signal for brain-machine interfacing is acquired on the basis of a frontal brainwave signal, and, thus, it is possible to recognize a user's higher-order multiple intention. Therefore, it is possible to classify various signals corresponding to the user's intentions.

Further, according to any one of the above-described aspects of the present disclosure, a brainwave signal corresponding to the case where the user directly imagines what he/she intends can be directly extracted from a prefrontal area and then used as a control signal for brain-machine interfacing, and, thus, it is possible to directly match the content of the user' thinking with a goal-orientation of BMI control.

Furthermore, according to any one of the above-described aspects of the present disclosure, a result of prefrontal-based brain-machine interfacing is feedback in real time to the user in order for the user to repeatedly or continuously perform a process of directly imagining an intention for achieving a certain goal, and, thus, the present disclosure can be used for functional or cognitive improvement of the frontal area and rehabilitation using neurofeedback.

Moreover, according to any one of the above-described aspects of the present disclosure, a signal from the frontal area with fewer hindrances to measurement of brainwave signals such as hair is used, and, thus, the efficiency and accuracy in acquiring brainwave signals can be increased. Further, the present disclosure can contribute to improve a progressive function of a non-invasive BMI system and can also be applied to an invasive BMI system.

Besides, according to any one of the above-described aspects of the present disclosure, brainwave measurement positions are checked through a 3D scanner, and, thus, it is possible to minimize an error which can be generated due to repeated measurement for each anatomical source position (due to the sensor position that is critical for source-localization) from which a prefrontal signal will be measured. Therefore, it is possible to increase the reliability and accuracy in extracting and classifying features of brainwave signals.

Also, according to any one of the above-described aspects of the present disclosure, a signal processing stage configured to process brainwave signals can be implemented as an integrated unit with a brainwave measurement device, and a brain-machine interfacing apparatus can perform wireless communication with an external device and thus can be used as a portable EEG-based BMI apparatus.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

FIG. 7 is a flowchart provided to explain a prefrontal-based cognitive brain-machine interfacing method in accordance with various embodiments described herein.

DETAILED DESCRIPTION

Figure 1:
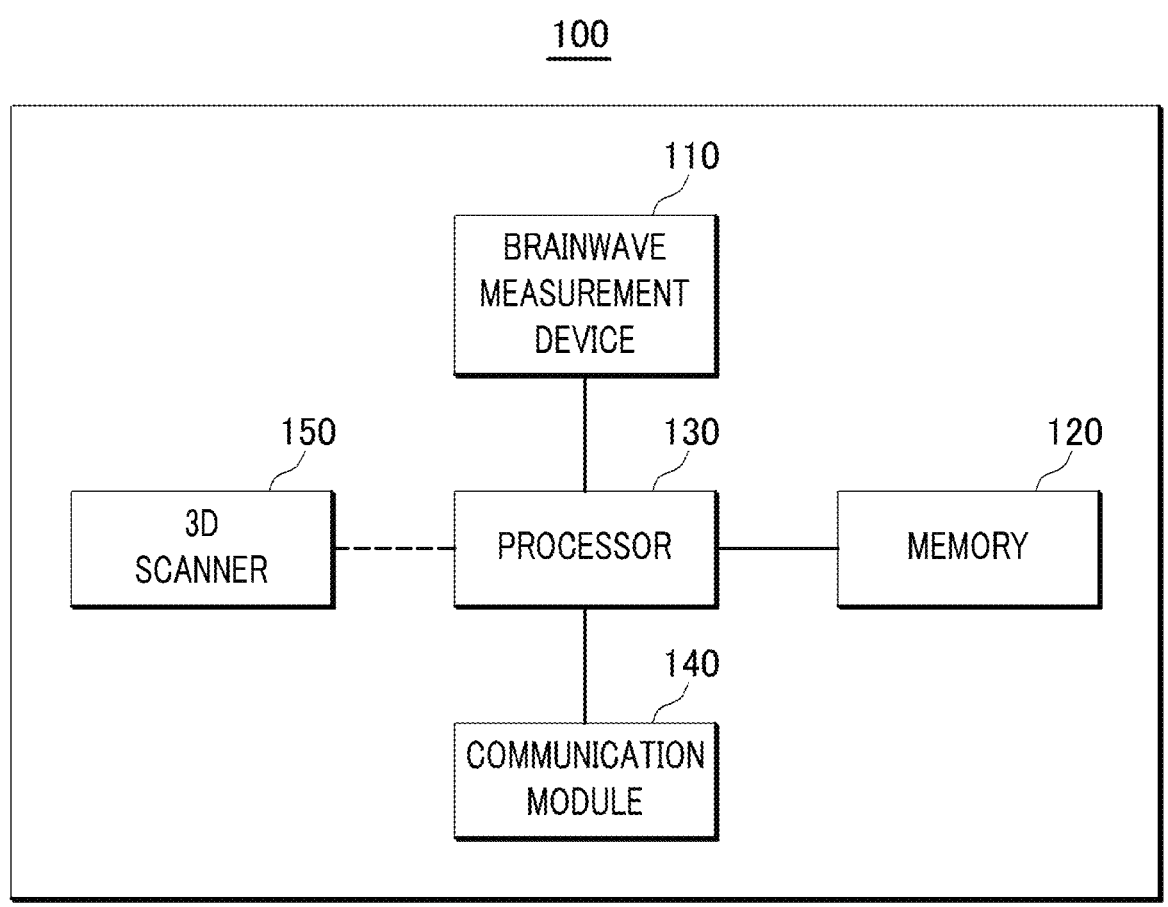
FIG. 1 is a configuration view of a prefrontal-based cognitive brain-machine interfacing apparatus in accordance with various embodiments described herein.

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, it is to be understood that the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "unit" or "module" includes a unit implemented by hardware or software and a unit implemented by both of them. One unit may be implemented by two or more pieces of hardware, and two or more units may be implemented by one piece of hardware.

FIG. 1 is a configuration view of a prefrontal-based cognitive brain-machine interfacing apparatus in accordance with an embodiment of the present disclosure.

A prefrontal-based cognitive brain-machine interfacing apparatus (hereinafter, abbreviated to "brain-machine interfacing apparatus" for convenience in explanation) 100 includes a brainwave measurement device 110, a memory 120, a processor 130, and a communication module 140.

Additionally, the brain-machine interfacing apparatus 100 according to an embodiment of the present disclosure may further include a 3D scanner 150 as illustrated in FIG. 1. In this case, the processor 130 of the brain-machine interfacing apparatus 100 may transmit and receive data to and from the 3D scanner 150 via wired or wireless communication through the communication module 140.

Prior to explanation about the components of the brain-machine interfacing apparatus 100, a prefrontal-based cognitive brain-machine interfacing process to be performed by the brain-machine interfacing apparatus 100 according to an embodiment of the present disclosure will be explained briefly with reference to FIG. 2 and FIG. 3.

Figure 2:
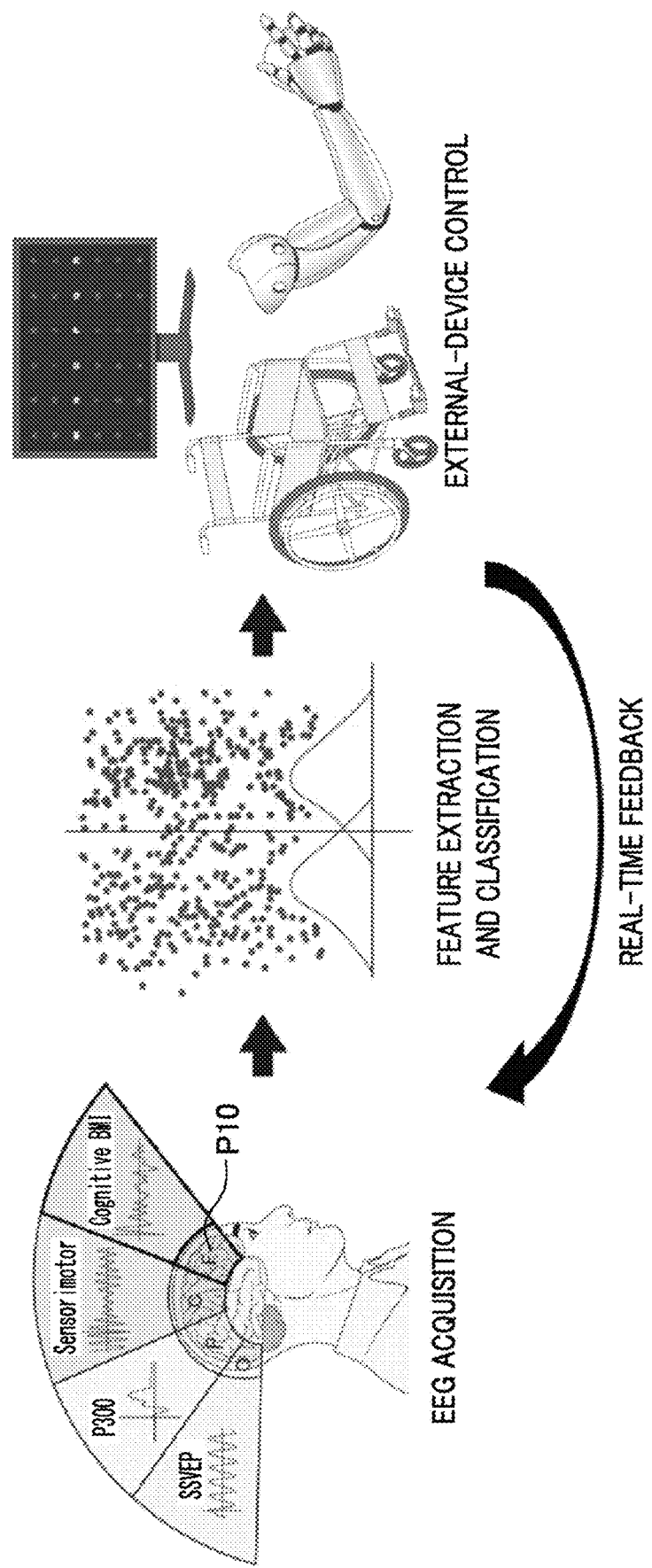
FIG. 2 is an example diagram provided to explain an overall concept of prefrontal-based cognitive brain-machine interfacing in accordance with various embodiments described herein.

FIG. 2 is an example diagram provided to explain an overall concept of prefrontal-based cognitive brain-machine interfacing in accordance with various embodiments described herein. Further, FIG. 3 is an example diagram provided to explain a difference between a prefrontal-based cognitive brain-machine interfacing (BMI) system in accordance with an embodiment of the present disclosure and a conventional motor imagery-based BMI system.

Referring to FIG. 2, the brain-machine interfacing apparatus 100 performs an "electroencephalogram (EEG) acquisition" process for extracting an EEG from a frontal area (particularly, prefrontal area) P10 in charge of decision-making, planning and evaluating ongoing actions, error-monitoring, intentional judgement, and the like. If BMI is driven on the basis of the acquired prefrontal EEG, the brain-machine interfacing apparatus 100 may perform an "external-device control" process for directly matching a subject's idea with an operation of an external device through BMI control. In this case, the brain-machine interfacing apparatus 100 performs a "feature extraction and classification" process on the basis of the acquired prefrontal EEG and performs external-device control on the basis of a result of the process. Thus, a result of regulating the external device is feedback in real time to the subject. Therefore, the subject can check a control status of the external-device directly corresponding to an intention that the subject imagines.

This paradigm of BMI control shows a "goal-oriented BMI" technology, and a brainwave signal that directly reflects the user's higher-order intention is used as a BMI control signal. A prefrontal brainwave signal is independent of peripheral sensory modalities such as sight, hearing, and touch, and contains only the subject's higher-order abstractive and cognitive intention. Therefore, a BMI control system using a prefrontal EEG is less affected by the modality of a BMI task that the subject needs to perform a goal-irrelevant task for specific control (e.g., action or imagination irrelevant to a preset intended direction of the apparatus).

Figure 3:
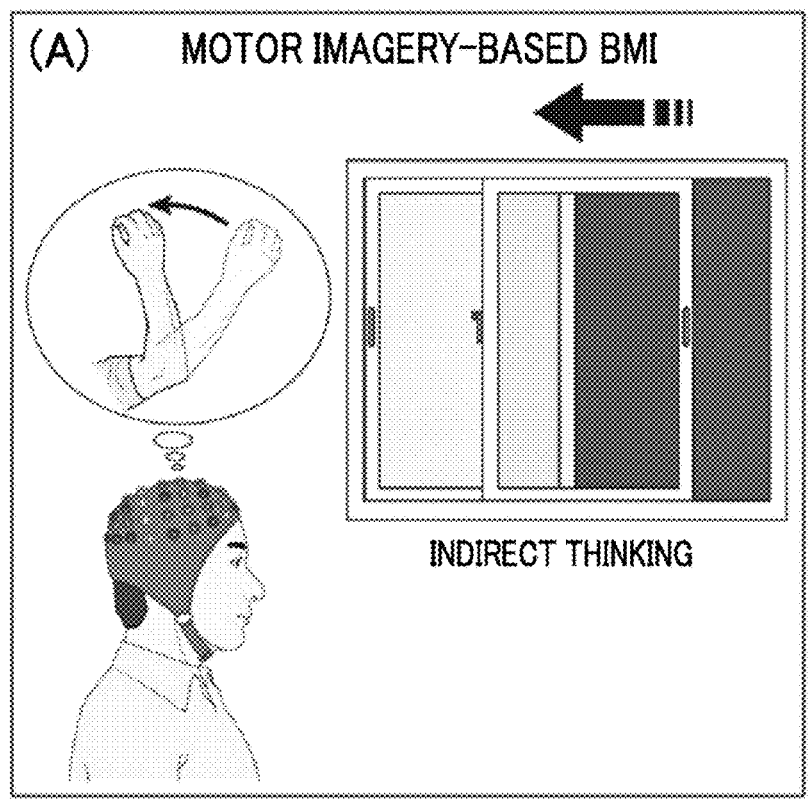
FIG. 3 is an example diagram provided to explain a difference between a prefrontal-based cognitive brain-machine interfacing (BMI) system in accordance with various embodiments described herein and a conventional motor imagery-based BMI system.
Figure 3:
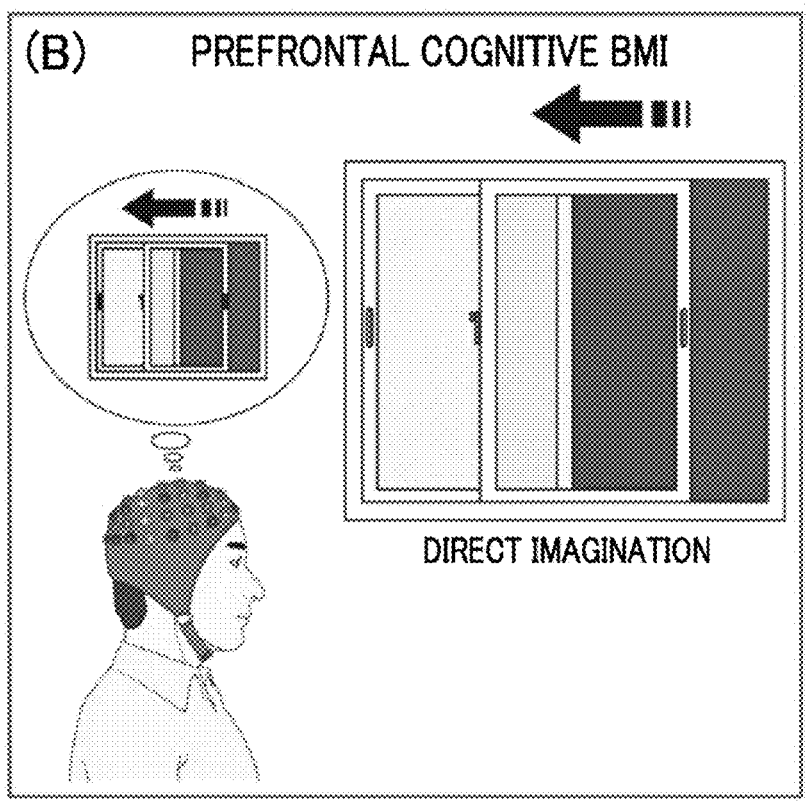

FIG. 3 shows an example of BMI control for opening a window to the left on the basis of an EEG.

An example illustrated in (A) of FIG. 3 shows the case of using a conventional cognitive BMI technology. In this case, an EEG corresponding to indirect thinking such as imagination about a movement of hands totally irrelevant to the action of opening the window is used for BMI control. For example, in a typical motor-imagery BMI technology, a movement-related cortical potential has been used as a BMI control signal.

An example illustrated in (B) of FIG. 3 shows the case of using a prefrontal-based cognitive BMI technology in accordance with an embodiment of the present disclosure. In this case, a prefrontal EEG is used for BMI control. That is, external-device on BMI system can be intuitively driven on the basis of a prefrontal brainwave signal that is generated when the user directly imagines opening the window.

Further, the prefrontal-based cognitive BMI may be applied to real-time neurofeedback in order to contribute to the rehabilitation of a patient with prefrontal damage or enhance the cognitive functioning of prefrontal brain region of a normal person. For example, if the user repeatedly imagines operations of an external device that he/she wants to control and the external device is controlled to perform an operation with content directly corresponding to the content of his/her imagination, it is possible to obtain a therapeutic effect in the rehabilitation for patients with obsession or ADHD. That is, the neural activity of the functionally or neurologically damaged prefrontal region can be continuously restored by neurofeedback, and, thus, it is possible to induce neurological rehabilitation and functional rehabilitation by neural plasticity of the corresponding brain region. Further, even in the case of a patient with damage to the occipital lobe or parietal lobe from which brainwaves are mainly acquired according to the conventional BMI technology, BMI can be driven using brainwaves generated from the intact prefrontal area.

Returning to FIG. 1, the configuration and the operation of the brain-machine interfacing apparatus 100 in accordance with an embodiment of the present disclosure will be described in detail.

The brainwave measurement device 110 measures an EEG from the subject. In this case, the brainwave measurement device 110 measures a sensor-level EEG of the subject.

The brainwave measurement device 110 can measure an EEG in a contact manner or non-contact manner, and the measurement method is not limited. Further, the brainwave measurement device 110 may be a brainwave measurement equipment itself including brainwave measurement units (e.g., electrodes for brainwave sensing, etc.) or may control the brainwave measurement equipment as being connected thereto to acquire a measured brainwave signal.

Figure 6:
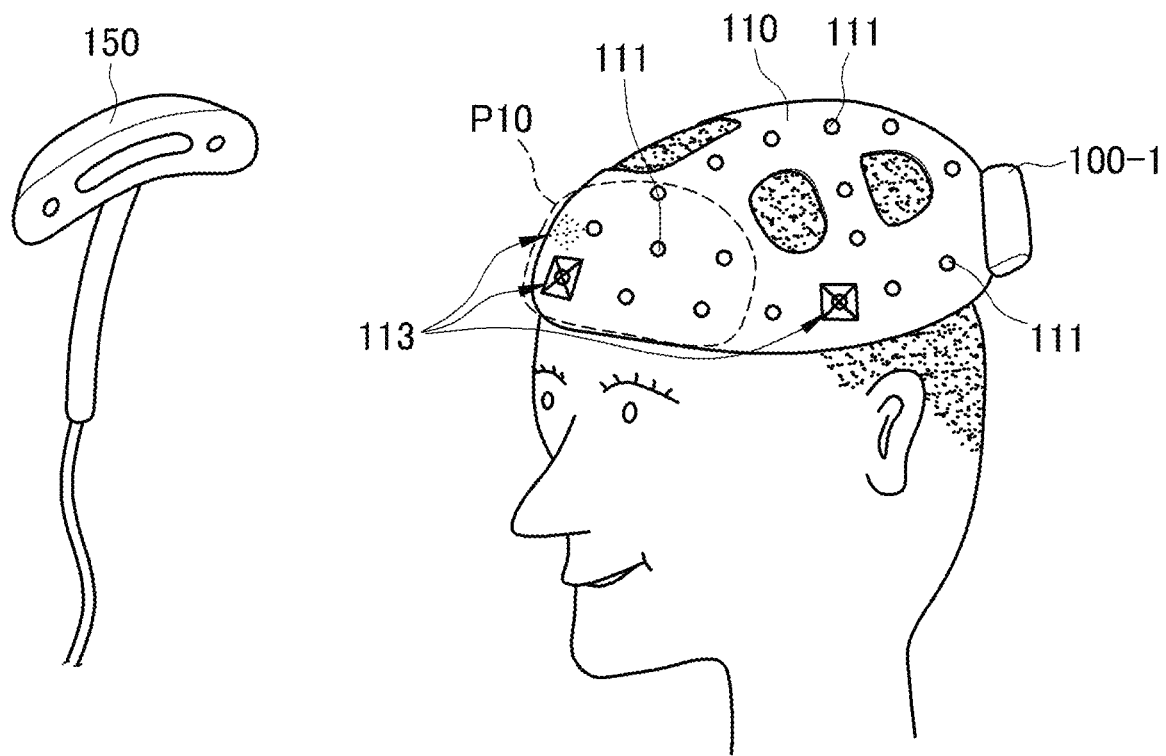
FIG. 6 is a configuration view provided to explain a device of a prefrontal-based cognitive brain-machine interfacing apparatus to check electrode attachment positions in accordance with various embodiments described herein.

For reference, as illustrated in FIG. 6, at least one component 100-1 of the brain-machine interfacing apparatus 100 may be implemented as integrated with the brainwave measurement equipment (illustrated as the brainwave measurement device 110 itself in FIG. 6). For example, the brainwave measurement device 110 may be implemented as a headset equipped with the brainwave measurement units (i.e., electrodes 111, etc.) at preset multiple positions.

The brainwave measurement device 110 can continuously measure the intensities of brainwaves from preset multiple brain regions, particularly targeting on the prefrontal area. In this case, the brainwave measurement units of the brainwave measurement device 110 may operate at positions corresponding to the preset multiple brain regions, respectively.

The memory 120 stores a cognitive brain-machine interface program configured to generate a BMI control signal depending on a direct intention of the subject on the basis of a prefrontal EEG based on the brainwave measurement device 110. The processes according to the cognitive brain-machine interface program will be described in detail with the processor 130.

The memory 120 collectively refers to a non-volatile storage device that retains information stored therein even when power is not supplied and a volatile storage device that requires power to retain information stored therein.

The processor 130 executes the program stored in the memory 120 to perform the processes according to the program.

Hereinafter, the processes performed by the processor 130 when the cognitive brain-machine interface program is executed will be described in detail with reference to FIG. 4 and FIG. 5.

Figure 4:
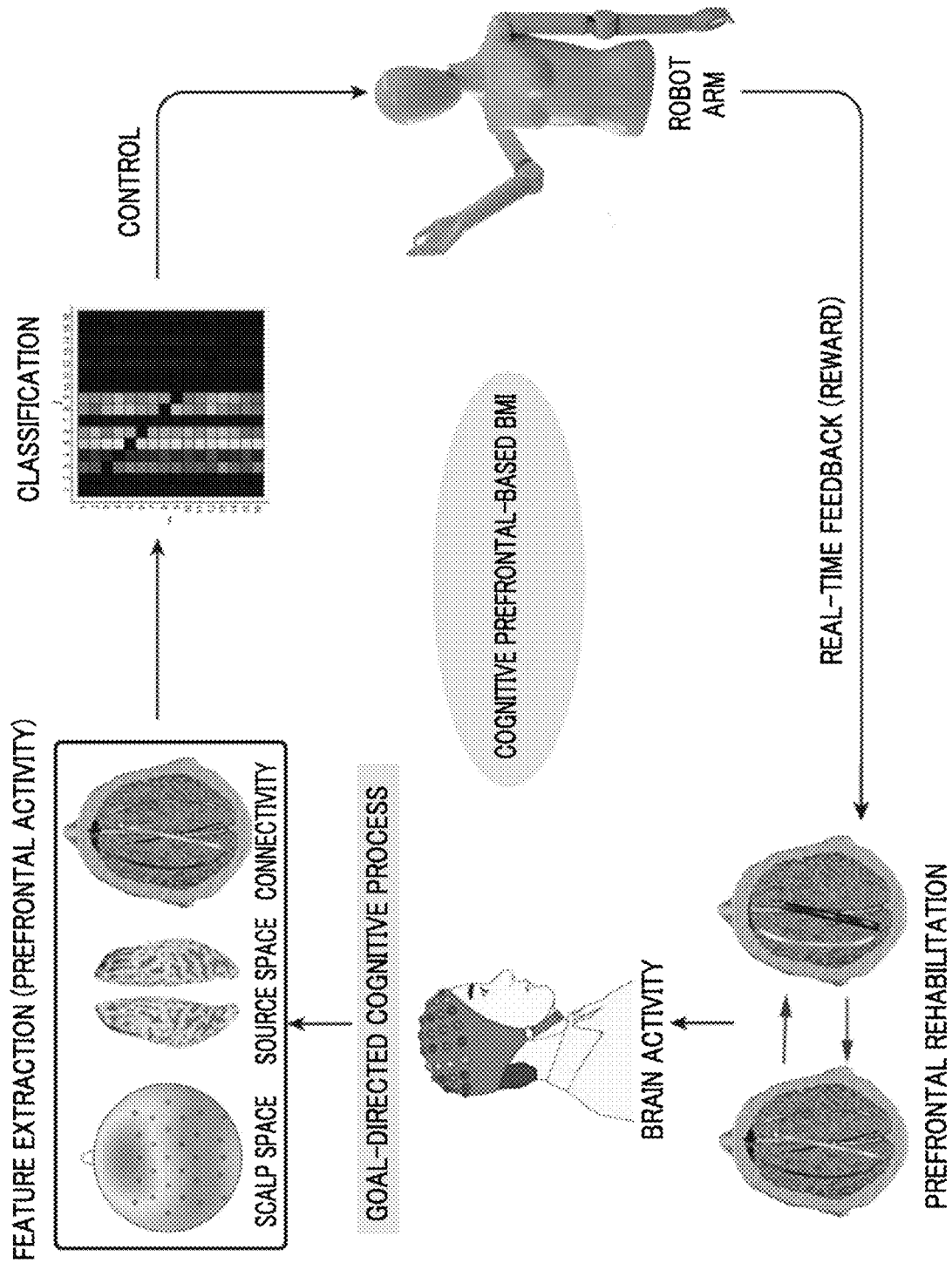
FIG. 4 is an example diagram provided to explain a prefrontal-based cognitive brain-machine interfacing process in accordance with various embodiments described herein.
Figure 5:
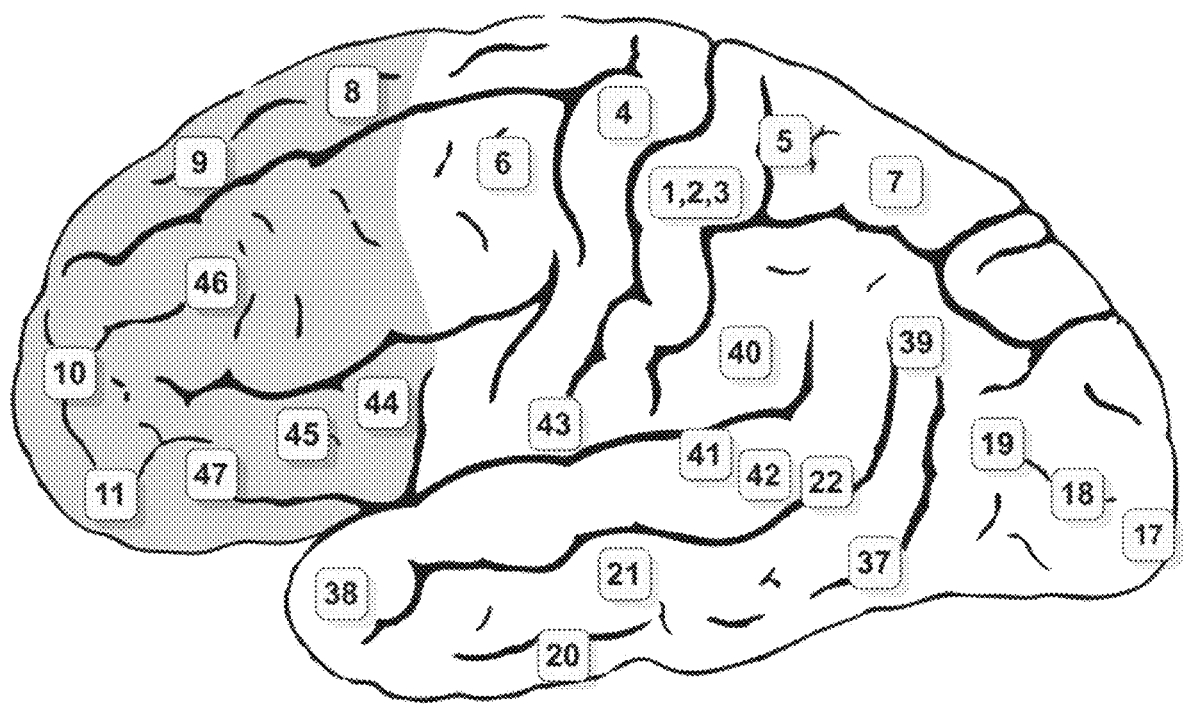
FIG. 5 is an example diagram of Brodmann area provided to explain brain regions from which brainwave signals are acquired in accordance with various embodiments described herein.

FIG. 4 is an example diagram provided to explain a prefrontal-based cognitive brain-machine interfacing process in accordance with an embodiment of the present disclosure. Further, FIG. 5 is an example diagram of Brodmann area provided to explain prefrontal regions from which brainwave signals are essential for BMI control in accordance with an embodiment of the present disclosure.

In an embodiment of the present disclosure, the measurement of an EEG by the brain-machine interfacing apparatus 100 through multiple electrodes (hereinafter, referred to as "sensor electrodes") attached to the scalp of the subject will be described. As illustrated in FIG. 4, the subject may wear a headset (i.e., the brainwave measurement device 110) in which sensor electrodes are arranged at multiple positions corresponding to preset brain regions, respectively.

In order to perform prefrontal-based BMI, it is important to accurately extract prefrontal brainwaves from corresponding anatomical areas and identify them. For example, in the prefrontal area, a dorsolateral prefrontal cortex (PFC) region (e.g., Brodmann area (BA) 9 and 46) is in charge of final analysis of non-emotional or dynamic information processing, and a ventromedial PFC region (e.g., BA 10, 11, 12, 13, 14, 25, and 32) is in charge of final analysis of emotional or static information processing. On this basis, the brain-machine interfacing apparatus 100 identifies the activities of different subdivisions of the prefrontal area and uses them for BMI control in a detailed manner.

In this case, the processor 130 analyzes an EEG measured at the scalp-level (sensor-level), later converted into cortical-level (source-level) in which a brainwave is generated, and uses a source-level activity of the tracked anatomical brain region as a BMI feature. The processor 130 pinpoints a brain cortical region generating the corresponding prefrontal brainwave signal among previously assigned multiple subdivisions of a prefrontal area.

The activities of various cortical regions of the brain cause electromagnetic activities of the respective scalp regions. Therefore, it is inferred that the activity of each scalp region is caused by composition and combination of various source-level activities. In general, a position for measurement of an EEG from the scalp as a result of a brainwave signal generated from the source in the brain is limited, but the backward calculation of the source of a brainwave on the basis of an EEG measured from the scalp is an "inverse problem" having infinite solutions. In order to solve this inverse problem, the processor 130 makes an optimized forwarding model from the source of a brainwave to a sensor electrode on the scalp, and on this basis, the processor 130 performs a backward calculation to obtain an optimal brainwave signal from the reasonable source positions required for BMI feature analysis. The processor 130 performs modeling of the optimized forward model to best identify a prefrontal signal from each anatomical subdivision with high spatial precision through the optimized forward model.

After receiving an EEG (hereinafter, referred to as "sensor-level signal") measured on the scalp of the subject from the brainwave measurement device 110, the processor 130 performs source-localization based on the sensor-level signals to convert the sensor-level (i.e., scalp-level) signal into a cortical level (i.e., source-level) PFC signal.

The processor 130 may calculate a PFC signal (i.e., source-level signal) from the cortical source corresponding to the sensor-level EEG signal from the scalp region using an inverse source-localization program in order to find out the source of a brainwave signal from its anatomical origin. The inverse source-localization program refers to a program for computing the degree of activity of the brain at the cortical level, and for example, a dipolar model and a distributed source model may be used.

Specifically, the processor 130 performs source-localization on the basis of sensor-level signals measured from the respective multiple scalp regions. Herein, as a method for the source-localization, low resolution electromagnetic tomography (LORETA) which is the distributed source model or a cortical current density source model may be used. Further, the processor 130 computes the degree of source activity as a result of EEG source-localization. That is, the processor 130 calculates activated brain source regions corresponding to sensor-level EEGs measured at the scalp of the subject and the degrees of activity of the respective regions.

The processor 130 may convert the EEG measured from the scalp of the subject into source-level brainwave signal in the Brodmann area in real time. For example, the processor 130 may divide the left/right prefrontal areas into five regions as shown in Table 1 to match the regions with preset brain cortical regions in the Brodmann area, and use the activities of the respective regions for BMI control. For reference, the respective regions in the Brodmann area refer to cortical regions grouped by type and feature of neurons, and cortical regions included in the same group in the Brodmann area may function identically or similarly to each other. Further, the positions of the prefrontal regions included in Table 1 are marked on the Brodmann area in FIG. 5. FIG. 5 is a side view of the brain as viewed from one side (e.g., left side), and omits some prefrontal regions at positions difficult to be directly illustrated (i.e., on the other side of the brain) for convenience.

TABLE 1

| Name | Brodmann Area and Functioning |
| --- | --- |
| Dorsolateral PFC | BA 9, 46 (Suppression, Manipulation, Monitoring, Sustained Attention, etc.) |
| Ventrolateral PFC | BA 44, 45 (Information Retrieval and Maintenance, Action Planning and Updating, etc.) |
| Ventromedial PFC | BA 12, 13, 14, 25, 32 (Decision-making, Emotion Control, etc.) |
| Anterior PFC | BA 10 (Multitasking, Intention Maintenance, etc.) |
| Orbitofrontal cortex | BA 11, 47 (Behavior Reinforcement and Emotion Control by Evaluation/Reward/Punishment, etc.) |

Further, the processor 130 extracts a Granger causality between brainwave signals from different brain regions (particularly centered at prefrontal region) as a brain signal feature (i.e., BMI feature) according to a higher-order intention of the subject on the basis of PFC signals.

A cognitive feature depending on the content imagined by the subject causes a significant difference in a prefrontal brainwave measured from the subject. Thus, a mainly activated brain region among the multiple prefrontal regions of the subject can be detected. In this case, the processor 130 selects two or more brain regions showing a Granger causality and extracts a brain signal feature. The processor 130 may select two or more brain regions showing the highest Granger causality in order of the most activated brain region (i.e., brain region with the highest activity).

Then, the processor 130 analyzes a time-dependent directional causality among the selected two or more brain regions and detects a Granger causality among the selected two or more brain regions. In this case, the processor 130 may detect a causal and functional connection by analyzing brainwave signals (i.e., PFC signals) from the selected two or more prefrontal regions by a Granger causality method.

For reference, Granger causality analysis makes it possible to determine whether there is a causality between two phenomena. Therefore, the processor 130 detects a directional causality (i.e., Granger causality) between two or more activated brain regions (particularly centered at prefrontal regions) of the subject through the Granger causality analysis. For example, the processor 130 may obtain the degree of Granger causality through a directed transfer function by using a multivariate autoregressive model with respect to EEGs acquired from the multiple sensor electrodes.

As for activated multiple source regions and a Granger causality between the activated source regions, the degree of causality can be indicated by a color of an arrow and the direction thereof may be indicated by a direction of the arrow as illustrated in FIG. 4. With the Granger causality method, a "directional causality (i.e., Granger causality)" between brain regions can be displayed in the form of a mosaic matrix. As shown in a stage "Classification" of FIG. 4, the degrees of Granger causality in a direction from j to i on the mosaic matrix are displayed in various colors. The numbers in the i-axis and j-axis on the mosaic matrix represent the respective regions in the Brodmann area.

As such, each Granger causality between brain regions activated corresponding to the imagination of the subject is displayed differently. For example, if the subject imagines a certain movement, a first brain region and a second brain region may be most activated and the order of activation may have a Granger causality with a certain directionality.

Further, if the subject imagines another movement, other brain regions different from the first and second brain regions may be most activated, or the same brain regions may be activated with different degrees of activity or different directionality. Therefore, each content imagined by the subject shows a different Granger causality feature (i.e., BMI feature).

As such, the processor 130 recognizes a brain activity pattern (related to prefrontal activity) depending on a Granger causality between brain regions. Further, the processor 130 identifies a preset BMI control movement on the basis of the recognized prefrontal-centered activity pattern.

Specifically, the processor 130 classifies extracted brain signal features into different BMI control signals through machine learning. In this case, the processor 130 may classify prefrontal signal features into different BMI control signals through machine learning such as LDA (linear discriminant analysis), SVM (Support Vector Machine), and deep-learning. For reference, the kind of machine learning used by the processor 130 as a classifier is not limited.

The processor 130 processes an operation as a kind of classifier and performs machine learning of a prefrontal activity pattern labelled for preset brainwave conditions (i.e., imagination of a subject about what he/she intends to do) for each of multiple subjects in advance. Then, the processor 130 identifies a prefrontal activity pattern depending on an EEG of a current subject through the machine-learned classifier and generates a control signal.

That is, prior to BMI control based on a higher-order cognitive feature of the subject by analyzing an EEG of the subject, the processor 130 performs an initial process for learning a prefrontal activity pattern of certain goals (i.e., goals to be achieved through BMI) for each of the multiple subjects. In this case, the processor 130 may perform machine learning of a feature extracted from a labeled training EEG measured from each subject to perform calibration for setting a standard value of the classifier. Further, the prefrontal activity patterns identified by the classifier may be matched with control signals for controlling operations of multiple external devices, respectively.

Thus, a higher-order brain signal feature corresponding to the content of the subject's imagination can be identified, and a control signal matched with the identified brain signal feature can be used as a BMI control signal (e.g., a preset machine control signal). Therefore, it is possible to increase the performance accuracy of BMI control. For example, the BMI (or BCI) task drives the mental processing that principally induces prefrontal activation.

Meanwhile, returning to FIG. 1, the brain-machine interfacing apparatus 100 may use the 3D scanner 150 to enhance the accuracy when converting an EEG measured from the scalp of the subject into a cortical-level brainwave signal with high spatial precision. This will be described in detail with reference to FIG. 6.

FIG. 6 is a configuration view provided to explain a device of a prefrontal-based cognitive brain-machine interfacing apparatus to check electrode attachment positions in accordance with an embodiment of the present disclosure.

Whenever a brainwave is measured, there may be a considerable variation in the brainwave measurement positions (i.e., positions of the scalp electrodes). This variation causes a decrease in accuracy when a sensor-level signal is converted into a source-level signal. Therefore, in order to minimize a variation in the measurement positions of the electrodes whenever a brainwave is measured, the brain-machine interfacing apparatus 100 performs 3D scanning of the electrodes and the entire head of the subject.

Referring to FIG. 6, the electrodes 111 are arranged for the best EEG acquisition of the frontal area P10 in the brainwave measurement device 110 in order to facilitate the extraction of a brain source signal. As shown in FIG. 6, the multiple electrodes 111 may also be disposed on the brain region besides the frontal area P10.

For example, the multiple electrodes 111 may be arranged on the brainwave measurement device 110 by applying, e.g., the 10-10 international system for EEG electrode placement. The 10-10 international system is a high-density EEG electrode placement method to equally arrange electrodes at a distance of 10% of the total length of each of a central line (first axis) connecting nasion and inion and a line (second axis) connecting both ears while passing the vertex on the head.

Further, three landmark electrodes 113 are attached to one or more preset sites on the brainwave measurement device 110 corresponding to a forehead, left/right temples, and the like in order for the 3D scanner 150 to recognize 3D coordinates of the multiple electrodes 111. Herein, the 3D scanner 150 can check or estimate the position of each of the electrodes 111 on the basis of distances and angles from the landmark electrodes 113.

The 3D scanner 150 scans the position of the head of the subject and the positions of the respective electrodes 111 and 113 of the brainwave measurement device 110 worn on the head of the subject and generates 3D coordinates of the respective electrodes 111 and 113 on the basis of the position of the head. Further, the 3D scanner 150 transfers the generated 3D coordinates to the processor 130.

When the processor 130 receives the 3D coordinates of the respective electrodes 111 and 113 from the 3D scanner 150, it checks whether or not the scanned positions of the respective electrodes 111 and 113 are identical with preset reference positions. Then, according to the result thereof, the processor 130 may output information (visual or audio information) through an output means (monitor, or the like, not illustrated).

For example, the electrode position check information may be information indicative of whether the electrodes 111 and 113 of the brainwave measurement device 110 are identical to the preset reference positions, respectively, and may be information that matches the 3D coordinates of the respective electrodes 111 and 113 with a 3D model of the head of the subject and visually shows them. The kind and the output method of the electrode position check information are not limited.

The processor 130 may set reference positions of the electrodes on the basis of a result of scanning the head of the subject. For example, the processor 130 may match a preset brain area model (e.g., Brodmann area model) with the 3D scanned head of the subject and set positions corresponding to respective preset brain regions on the brain area model as reference positions. Further, the processor 130 may set reference positions on the basis of positions of brainwave measurement initially taken to the subject, positions of brainwave measurement taken during an initial process of learning a prefrontal activity pattern, or positions of the latest brainwave measurement.

The processor 130 may perform brainwave measurement for correcting the positions of the electrodes before brainwave measurement for BMI control to minimize a variation in the positions of the electrodes during repeated brainwave measurement. In this case, the processor 130 may output a control signal to repeat brainwave measurement until the positions of the electrodes of the brainwave measurement device 110 are identical to the reference positions. After it is confirmed that the positions of the electrodes of the brainwave measurement device 110 are identical to the reference positions, brainwave measurement and analysis for actual BMI control may be performed.

Since it is checked whether or not the positions of electrodes during brainwave measurement for BMI control are identical with the reference positions as described above, it is possible to suppress any problem caused by a variation in the positions of the electrodes during EEG source-localization. Further, such a process of fixing the positions may be used for neuroimaging co-registration.

Meanwhile, as illustrated in FIG. 6, the brain-machine interfacing apparatus 100 according to an embodiment of the present disclosure may be provided as a device separate from the 3D scanner 150. In this case, the brain-machine interfacing apparatus 100 may be implemented as the portable brainwave measurement device 110 equipped with the other components (i.e., including the memory 120, the processor 130, and the communication module (e.g., communication circuit) 140 and hereinafter referred to as a brainwave analyzing unit 100-1) as a kind of real-time signal analyzing device.

For example, the brainwave analyzing unit 100-1 may be implemented as hardware configured to wiredly or wirelessly transmit a control signal generated on the basis of real-time activity for each prefrontal region in the Brodmann area to a BMI device (i.e., external-device) through the communication module 140. In this case, the brainwave analyzing unit 100-1 may be mounted, for example, on the occipital region of the brainwave measurement device 110.

The brain-machine interfacing apparatus 100 can link to various BMI devices. For example, a door lock which is one of security devices may be applied as a BMI device linked to the brain-machine interfacing apparatus 100. For reference, the door lock may include a means (not illustrated) for unlocking and locking a door, and may further include a control module (not illustrated) for controlling an operation of the unlocking/locking means and a communication module (not illustrated) for data transmission with the processor 130 of the brain-machine interfacing apparatus 100. In this case, if the subject imagines a specific series of numbers or letters for the door lock (e.g., conceiving a password for the door lock), a prefrontal activity pattern is extracted by analyzing an EEG measured from the scalp of the subject in response to the imagination. Then, the extracted prefrontal activity pattern is identified through a machine-learned classifier to generate a control signal corresponding thereto. If the subject imagines unlocking the door lock, the brain-machine interfacing apparatus 100 may transmit a control signal to operate in a mode to receiving information for unlocking to the door lock. Then, if the subject sequentially imagines numbers of the password for the door lock, the brain-machine interfacing apparatus 100 may sequentially transmit the numbers to the door lock to unlock the door lock.

The BMI device linked to the brain-machine interfacing apparatus 100 may include a robot having a communication function (e.g., communication circuit), a smartphone, etc., and the kind thereof is not limited. The kind of a control signal for controlling the BMI device is not limited, either.

Hereinafter, a prefrontal-based cognitive brain-machine interfacing method in accordance with an embodiment of the present disclosure will be described with reference to FIG. 7.

FIG. 7 is a flowchart provided to explain a prefrontal-based cognitive brain-machine interfacing method in accordance with an embodiment of the present disclosure.

The prefrontal-based cognitive brain-machine interfacing method to be described below may be performed by the processor 130 of the brain-machine interfacing apparatus 100 described above.

Before prefrontal brainwave signal-based BMI control is performed, the subject's brainwave signal measured by the brainwave measurement device 110 is input in a state where a specific intention (i.e., higher-order intention) imagined by the subject is already known. As such, the measured brainwave signal is labelled for the intention imagined by the subject. Then, a signal feature is extracted on the basis of the labeled training EEG. In this case, two or more most activated prefrontal regions are detected on the basis of the labeled training EEG, and a Granger causality between the detected brain regions is extracted as a prefrontal activity pattern. Then, a classifier for the prefrontal activity pattern is generated by machine-learning (supervised or unsupervised machine learning) of extracted prefrontal activity patterns.

Further, as illustrated in FIG. 7, during prefrontal brainwave signal-based BMI control, a sensor-level (scalp-level) brainwave signal (i.e., EEG) is measured from the subject who is directly imagining an intention (S710).

Then, an anatomical source activity that generates a scalp-level brainwave is computed (S720).

Then, a feature of a higher-order cognitive EEG (i.e., prefrontal activity pattern) is extracted on the basis of the activity of each tracked (source-localized) brain region (i.e., prefrontal region) (S730).

In this case, source-localization is performed to a sensor-level EEG signal to convert the sensor-level signal into a source-level signal (i.e., PFC signal). Then, activated prefrontal regions are detected on the basis of the degrees of activity of the source-level signals, and two or more brain regions showing the highest Granger causality are selected in order of the most activated brain region to detect a Granger causality. As such, a directional Granger causality among the selected two or more brain regions may be extracted as a prefrontal activity pattern.

Then, the extracted brain region activity pattern (i.e., prefrontal activity pattern) is input into the machine-learned classifier to identify a feature corresponding to the EEG feature from among preset BMI control conditions (S740).

Then, a control signal (e.g., a preset machine regulating signal) according to a result of classification performed in the process S740 is generated and output (S750).

That is, a BMI control condition directly corresponding to the content of the previously labeled intention of the subject is identified and then, a control signal for implementing the content of the subject's intention is transmitted to a corresponding BMI device.

Meanwhile, in the prefrontal-based cognitive brain-machine interfacing method in accordance with an embodiment of the present disclosure, a process for checking the positions of electrodes may be performed by the 3D scanner 150 before the process S710. The process for checking the positions of electrodes is identical or similar to the process described above with reference to FIG. 6.

The above-described prefrontal-based cognitive brain-machine interfacing method in accordance with an embodiment of the present disclosure can be embodied in a storage medium including instruction codes executable by a computer such as a program module executed by the computer. A computer-readable medium can be any usable medium which can be accessed by the computer and includes all volatile/non-volatile and removable/non-removable media. Further, the computer-readable medium may include all computer storage and communication media. The computer storage medium includes all volatile/non-volatile and removable/non-removable media embodied by a certain method or technology for storing information such as computer-readable instruction code, a data structure, a program module or other data. The communication medium typically includes the computer-readable instruction code, the data structure, the program module, or other data of a modulated data signal such as a carrier wave, or other transmission mechanism, and includes a certain information transmission medium.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A prefrontal-based cognitive brain-machine interfacing apparatus, comprising:
    a brainwave measurement device configured to measure a prefrontal brainwave signal of a subject;
    a memory in which a cognitive brain-machine interface program is stored; and
    a processor configured to execute the program stored in the memory,
    wherein upon execution of the cognitive brain-machine interface program, the processor pinpoints a brain cortical region corresponding to the prefrontal brainwave signal among previously assigned multiple subdivisions of a prefrontal area, measures a degree of corresponding brain activities, extracts a prefrontal activity pattern by measuring the degree of corresponding brain activities and calculating causal connectivity among two or more previously assigned brain regions based on a corresponding sensor-level brain activity, inputs the extracted prefrontal activity pattern into a classifier which is previously generated by machine learning of multiple prefrontal activity patterns of the subject to identify any of preset control conditions corresponding to the extracted prefrontal activity pattern among preset brain-machine interface control conditions, and generates and outputs a machine regulating signal corresponding to one of the preset control conditions identified by the classifier, and
    the classifier is generated by machine learning of the prefrontal activity patterns labelled for contents of multiple intentions, respectively, based on the prefrontal brainwave signals of the subject.

2. The prefrontal-based cognitive brain-machine interfacing apparatus of claim 1,
    wherein the processor performs source-localization to an electroencephalogram (EEG) measured from the subject to convert the EEG into a prefrontal cortex (PFC)

signal, and detects a degree of activity of the PFC signal in each individual subdivision of the prefrontal area.

3. The prefrontal-based cognitive brain-machine interfacing apparatus of claim 2,
wherein the processor converts the EEG into a cortical-level brainwave signal in a Brodmann area and detects a brain region corresponding to the converted brainwave signal from among preset brain regions in the Brodmann area, and
the preset brain regions in the Brodmann area include dorsolateral PFC, ventrolateral PFC, ventromedial PFC, anterior PFC, and orbitofrontal cortex.

4. The prefrontal-based cognitive brain-machine interfacing apparatus of claim 1,
wherein the processor computes the causal connectivity by calculating a time-dependent directional causality among brainwave signals of two or more brain regions by a Granger causality method.

5. The prefrontal-based cognitive brain-machine interfacing apparatus of claim 4, further comprising:
a 3D scanner configured to generate 3D coordinates of respective electrodes for the brainwave measurement device when said brainwave measurement device is worn on the subject; and
a communication module configured to transmit and receive data to and from external devices including the 3D scanner,
wherein the processor checks whether the 3D coordinates of the respective electrodes for brainwave measurement are identical to preset reference positions of the respective electrodes for brainwave measurement and outputs a result of checking positions of the electrodes, and
the respective electrodes are respectively arranged at multiple positions corresponding to preset brain regions in the brainwave measurement device.

6. The prefrontal-based cognitive brain-machine interfacing apparatus of claim 5,
wherein the memory, the processor, and the communication module are provided as integrated with the brainwave measurement device, and
wherein the 3D coordinates and a result of 3D scanning the head are received through the communication module via wired or wireless communication with the 3D scanner.

7. A prefrontal-based cognitive brain-machine interfacing method by a prefrontal-based cognitive brain-machine interfacing apparatus, comprising:
receiving a prefrontal brainwave signal of a subject from a brainwave measurement device;
pinpointing a cortical-level brain region corresponding to the prefrontal brainwave signal measured by the brainwave measurement device among previously assigned multiple subdivisions of a prefrontal area;
extracting a prefrontal cortical-level activity pattern by computing source localization and calculating causal connectivity among two or more previously assigned brain regions on the basis based on a degree of corresponding sensor-level brain activity;
inputting the extracted prefrontal activity pattern into a classifier which is previously generated by machine learning of multiple prefrontal activity patterns of the subject to identify any of preset control conditions corresponding to the extracted prefrontal activity pattern among preset brain-machine interface control conditions; and
generating and outputting a machine regulating signal corresponding to one of the preset control conditions identified by the classifier,
wherein the classifier is generated by machine learning of the prefrontal activity patterns labelled for contents of multiple intentions, respectively, based on the prefrontal brainwave signals of the subject.

8. The prefrontal-based cognitive brain-machine interfacing method of claim 7,
wherein the pinpointing the cortical-level brain region includes:
performing source-localization to an electroencephalogram (EEG) measured from the subject to convert the EEG into a source-level prefrontal cortex (PFC) signal.

9. The prefrontal-based cognitive brain-machine interfacing method of claim 8,
wherein the performing source-localization includes:
converting the EEG into a brainwave signal in a Brodmann area; and
detecting a brain region corresponding to the converted brainwave signal from among preset brain regions in the Brodmann area, and
wherein the preset brain regions in the Brodmann area include dorsolateral PFC, ventrolateral PFC, ventromedial PFC, anterior PFC, and orbitofrontal cortex.

10. The prefrontal-based cognitive brain-machine interfacing method of claim 8,
wherein the performing source-localization is implemented by, at least one of low resolution electromagnetic tomography (LORETA) and a cortical current density source model.

11. The prefrontal-based cognitive brain-machine interfacing method of claim 8,
wherein the extracting the prefrontal activity pattern includes:
detecting a degree of activity of the source-level PFC signal; and
computing the causal connectivity by calculating a time-dependent directional causality among brainwave signals of two or more brain regions by a Granger causality method.

12. The prefrontal-based cognitive brain-machine interfacing method of claim 11, wherein the causal connectivity is obtained through a directed transfer function by using a multivariate autoregressive model.

13. The prefrontal-based cognitive brain-machine interfacing method of claim 11,
wherein the computing the causal connectivity includes:
sequentially selecting two or more brain regions showing a highest causal connectivity in order of a most activated brain region based on degrees of activity of respective brain regions.

14. The prefrontal-based cognitive brain-machine interfacing method of claim 7,
wherein multiple electrodes for brainwave measurement are respectively arranged at multiple positions corresponding to preset brain regions in the brainwave measurement device, and before the receiving the prefrontal brainwave signal of the subject, the prefrontal-based cognitive brain-machine interfacing method further comprises:
receiving 3D coordinates of the respective electrodes for brainwave measurement as a result of 3D scanning the brainwave measurement device, said brainwave measurement device being worn on the head of the subject, from a previously linked 3D scanner;

checking whether the 3D coordinates of the respective electrodes for brainwave measurement are identical to preset reference positions of the respective electrodes for brainwave measurement; and outputting electrode position check information based on a result of the checking.

\* \* \* \* \*